US011887706B1

(12) United States Patent
McNair

(10) Patent No.: US 11,887,706 B1
(45) Date of Patent: *Jan. 30, 2024

(54) BIT VECTOR RECORD LINKAGE

(71) Applicant: CERNER INNOVATION, INC., Kansas City, KS (US)

(72) Inventor: Douglas S. McNair, Seattle, WA (US)

(73) Assignee: Cerner Innovation, Inc., Kansas City, MO (US)

(*) Notice: Subject to any disclaimer, the term of this patent is extended or adjusted under 35 U.S.C. 154(b) by 750 days.

This patent is subject to a terminal disclaimer.

(21) Appl. No.: 17/072,601

(22) Filed: Oct. 16, 2020

Related U.S. Application Data

(60) Continuation of application No. 16/112,463, filed on Aug. 24, 2018, now Pat. No. 10,847,257, which is a division of application No. 14/505,855, filed on Oct. 3, 2014, now Pat. No. 10,096,381.

(60) Provisional application No. 61/886,457, filed on Oct. 3, 2013.

(51) Int. Cl.
 *G16H 10/60* (2018.01)
 *G16H 50/70* (2018.01)

(52) U.S. Cl.
 CPC ............ *G16H 10/60* (2018.01); *G16H 50/70* (2018.01)

(58) Field of Classification Search
 None
 See application file for complete search history.

(56) References Cited

U.S. PATENT DOCUMENTS

| 10,096,381 | B1 * | 10/2018 | McNair | G16H 50/70 |
| 10,249,385 | B1 * | 4/2019 | McNair | G16H 10/60 |
| 10,431,336 | B1 * | 10/2019 | Murrish | G16H 50/20 |
| 10,734,115 | B1 * | 8/2020 | McNair | G16H 50/30 |
| 11,348,667 | B2 * | 5/2022 | Hoffman | G16H 10/60 |
| 2007/0214016 | A1 | 9/2007 | Bennett et al. | |
| 2007/0214061 | A1 | 9/2007 | Toyokawa et al. | |

(Continued)

FOREIGN PATENT DOCUMENTS

| WO | 2011/077353 A2 | 6/2011 | |
| WO | WO-2011077353 A2 * | 6/2011 | G16H 20/00 |

OTHER PUBLICATIONS

Guha, et al. "Computational Approaches in Cheminformatics and Bioinformatics," 2012, John Wiley and Sons, Inc., Hobken, New Jersey, 264 pages.

(Continued)

*Primary Examiner* — Robert W Morgan
*Assistant Examiner* — Edward B Winston, III
(74) *Attorney, Agent, or Firm* — Invoke

(57) ABSTRACT

Methods, systems, and computer-readable media are provided for facilitating record matching and entity resolution and for enabling improvements in record linkage. A power-spectrum-based temporal pattern-specific weight may be incorporated into record linkage methods to enhance the record linkage accuracy and statistical performance. For example, in embodiments, a value-specific weight may be calculated from a population-based frequency of field-specific values or dichotomized values of selected phenotypic variables, and provides an opportunity to capture and measure the relative importance of specific values found in a field. A phenotypic bit-vector "fingerprint" pattern-specific weight or Bayesian power spectrum weight may be determined and incorporated into record linkage methods.

20 Claims, 11 Drawing Sheets

(56) References Cited

U.S. PATENT DOCUMENTS

2012/0203576 A1* 8/2012 Bucur .................... G16H 10/60
 705/3
2013/0035871 A1* 2/2013 Mayou ................... G16H 50/20
 702/26
2018/0374563 A1 12/2018 Douglas

OTHER PUBLICATIONS

Faulon, et al., "Handbook of Chemoinformatics Algorithms," 2010, Taylor and Francis Group, LLC, Boca Raton, FL, 440 pages.
Khoshhal et al., "Probabilistic LMA-based Classification of Human Behaviour Understanding Using Power Spectrum Technique", 13th Conference on Information Fusion (FUSION), Jul. 28-29, 2010, 10 pages.

* cited by examiner

| fn_c1 | fn_c2 | ln_c1 | ln_c2 | by | bm | bd | v1 | v2 | v3 | v4 | rl_wt | ps_wt | RMS(rl,ps) |
|---|---|---|---|---|---|---|---|---|---|---|---|---|---|
| MICHAEL | #N/A | MEYER | #N/A | 1988 | 1 | 31 | 225 | 200 | 168 | 187 | 0.8258 | 0.9250 | 0.8768 |
| MICHAEL | #N/A | MYER | #N/A | 1988 | 1 | 31 | 59 | 96 | 122 | 60 | 0.6779 | 0.8250 | 0.7550 |
| MICHAEL | #N/A | MAYER | #N/A | 1988 | 1 | 30 | 51 | 71 | 1 | 1 | 0.5244 | 0.8750 | 0.7213 |
| MICHAEL | #N/A | KUEHN | #N/A | 1943 | 10 | 9 | 3 | 4 | 4 | 3 | 0.1574 | 0.9750 | 0.6984 |
| MICHAEL | #N/A | MEIER | #N/A | 1988 | 1 | 9 | 120 | 152 | 74 | 141 | 0.5244 | 0.7250 | 0.6327 |
| MICHAEL | #N/A | KELLER | #N/A | 1965 | 3 | 19 | 78 | 34 | 115 | 63 | 0.1574 | 0.7750 | 0.5592 |
| MICHAEL | #N/A | VOGEL | #N/A | 1967 | 8 | 26 | 275 | 47 | 260 | 13 | 0.1574 | 0.6750 | 0.4901 |
| MICHAEL | #N/A | SCHAEFER | #N/A | 1991 | 5 | 30 | 301 | 156 | 78 | 172 | 0.1574 | 0.6250 | 0.4557 |
| MICHAEL | #N/A | FISCHER | #N/A | 1951 | 7 | 1 | 39 | 224 | 14 | 307 | 0.1574 | 0.5750 | 0.4215 |
| MICHAEL | #N/A | HAHN | #N/A | 1971 | 2 | 27 | 315 | 209 | 367 | 420 | 0.1574 | 0.5250 | 0.3876 |
| DIETER | #N/A | MEYER | #N/A | 1967 | 6 | 16 | 266 | 467 | 496 | 348 | 0.1479 | 0.4750 | 0.3518 |
| MANFRED | #N/A | MEYER | #N/A | 1959 | 10 | 12 | 328 | 245 | 361 | 91 | 0.1479 | 0.4250 | 0.3182 |
| STEFAN | #N/A | MEYER | #N/A | 1960 | 2 | 23 | 602 | 728 | 301 | 159 | 0.1479 | 0.3750 | 0.2850 |
| KLAUS | #N/A | MEIER | #N/A | 1983 | 11 | 10 | 427 | 242 | 444 | 675 | 0.1479 | 0.3250 | 0.2525 |
| THOMAS | #N/A | MAIER | #N/A | 1941 | 4 | 5 | 364 | 5 | 54 | 1 | 0.1479 | 0.2750 | 0.2208 |
| ANDREAS | #N/A | MAYER | #N/A | 1959 | 12 | 24 | 43 | 206 | 391 | 454 | 0.1479 | 0.2250 | 0.1904 |
| GERHARD | #N/A | MEYER | #N/A | 1941 | 11 | 25 | 465 | 255 | 94 | 14 | 0.1479 | 0.1750 | 0.1620 |
| JUERGEN | #N/A | MEIER | #N/A | 1983 | 7 | 7 | 582 | 370 | 369 | 48 | 0.1479 | 0.1250 | 0.1369 |
| UWE | #N/A | MEIER | #N/A | 1942 | 9 | 20 | 111 | 418 | 727 | 642 | 0.1479 | 0.0750 | 0.1173 |
| CARSTEN | #N/A | MEIER | #N/A | 1949 | 7 | 22 | 29 | 554 | 582 | 531 | 0.1479 | 0.0250 | 0.1061 |

*FIG. 3.*

|       | CR3T | HB1T  | K3T   | ALT3T | ALK3T | ALB1T |
|-------|------|-------|-------|-------|-------|-------|
| CR3T  |      | -0.01 | -0.05 | -0.29 | 0.09  | -0.11 |
| HB1T  |      |       | -0.08 | 0.16  | 0.35  | 0.45  |
| K3T   |      |       |       | 0.11  | 0.01  | -0.08 |
| A;T3T |      |       |       |       | 0.25  | 0.20  |
| ALK3T |      |       |       |       |       | 0.38  |
| ALB1T |      |       |       |       |       |       |

*FIG. 6A.*

|  | BD6 | BD2A | BD3B | BD3C |
|---:|:---:|:---:|:---:|:---:|
| MEDIAN | 0.33 | 0.50 | 0.33 | 0.33 |
| MEAN | 0.30 | 0.30 | 0.31 | 0.30 |
| CV% | 74.6% | 107.1% | 82.1% | 110.9% |
| SKEWNESS | 0.33 | 0.60 | 0.35 | 0.68 |
| KURTOSIS | -0.87 | -0.62 | -0.57 | -0.81 |

*FIG. 6B.*

```
library(fingerprint)
set.seed(1237)

# read encounters 6-elt bitmaps
# fp.read.to.matrix and fp.read are buggy in current release, except for some of the chemoinformatic
signatures like cdk.If
fpa <- as.data.frame(read.csv(file="C:/0_cerdsm/IP/MPI_rec_linkage_kullback_leibler/
fp6actives01.csv", header=FALSE))
fpb <- as.data.frame(read.csv(file="C:/0_cerdsm/IP/MPI_rec_linkage_kullback_leibler/fp6bg.csv",
header=FALSE))

# threshold for dichotomizing continuous data
s <- 0.55 functions for generating binary bit-vector fingerprints
ds <- function(x,t,j){
    if (x > t) return(j) else return(0)
  } dsfp <- function(x){
    if (is.null(x))
       return(new("fingerprint", nbit=6, bits=rep(0,6)))
    else
       return(new("fingerprint", nbit=6, bits=x))
    } initialize data frames to contain active (to-be-matched encounter) and background (candidate
encounters for person-level matches from RL)
fpla <- data.frame()
fplb <- data.frame()

# construct bit-set index vectors from active and background bitmaps
for (j in 1:length(fpa[,1])){
  bset <- NULL
  for (i in 1:6){
    b <- ds(fpa[j,i],s,i)
    if (b > 0) bset <- c(bset,b)
  }
  fpla <- append(fpla, list(bset))
} for (j in 1:length(fpb[,1])){
  bset <- NULL
  for (i in 1:6){
    b <- ds(fpb[j,i],s,i)
    if (b > 0) bset <- c(bset,b)
  }
  fplb <- append(fplb, list(bset))
}
```

.
.
.

*FIG. 7A*  Continues in FIG. 7B

Continues FROM FIG. 7A

.
.
.

```
# generate fingerprints for active and for background
# calculate pairwise modified Tanimoto distance
#  4.4 msec per distance call; 0.4 msec per dsfp call; 145 msec per append
# production version pre-allocates back list, process back once at solver init,
# and hold back var in cache memory of distance solver agent, 40 sec per 100K dsfp
# 10K-item partitions take 44 sec per partition to compute mt dist
dist <- rep(NA,length(fplb[]))
back <- list()
active <- new("fingerprint", nbit=6, bits=fpla[[1]])
for (k in 1:length(fplb[])){
  cmp <- dsfp(fplb[[k]])
  back <- append(back,cmp)
  dist[k] <- distance(active, cmp, method='mt')
} finds 1,019  (1.02%) out of 100,000 that have dist=1.0
5,988  (5.99%)                 dist>0.7
#     11,538 (11.54%)                 dist>0.6
# 12 instantiated dist values (0.000,0.079,0.148,0.200,0.208,0.259,0.321,0.452,0.500,0.625,0.706,1.000)
# statically reject any that are < 0.60 unless trauma may have acutely deranged the patient's values
# modified Tanimoto metric is a similarity metric and so distance can be obtained by subtracting dist
value fom 1.0 optionally weight distances per person by 50% lower prediction interval
distbar - max(0,0.67*SD*sqrt(1 + 1/N)) on a per-patient basis in background
dynamically reject background match candidates that are outside 50% LPI compute bit importance in background w.r.t. actives (subsecond)
all bits that are uniformly identical-valued (all-0s; all-1s) in all active and background exemplars get
NA in bit.importance
# This method evaluates the Kullback-Leibler (KL) divergence to rank the individual bits in a binary
# fingerprint in their ability to discriminate between background and actives. This method is
# implemented based on Nisius and Bajorath and includes an m-estimate correction.
# bi0 <- bit.importance(actives=list(active), background=back)
# bi0
[1] 0.062 0.060 0.068 0.254 0.067 0.302 compute spectrum of background set  (subsecond)
plausibly, bit.spectrum might be post-processed to represent predominantly set bits
# compare to fp's in hashed subsets that are similar
# bs0 <- bit.spectrum(back)
# bs0 <- bit.spectrum(active)
# [1] 0.303 0.298 0.326 0.307 0.320 0.259
```

FIG. 7B

BIT VECTOR RECORD LINKAGE

CROSS-REFERENCE TO RELATED APPLICATIONS

This application is a continuation application of U.S. application Ser. No. 16/112,463, filed Aug. 24, 2018, entitled "BIT VECTOR RECORD LINKAGE," which is a divisional application of U.S. application Ser. No. 14/505,855, filed Oct. 3, 2014, entitled "BIT VECTOR RECORD LINKAGE," which claims the benefit of U.S. Provisional Application No. 61/886,457 titled "BIT VECTOR RECORD LINKAGE," filed Oct. 3, 2013, each of which is hereby expressly incorporated by reference in its entirety.

INTRODUCTION

In the practice of administering health care, patient records concerning a single patient may be collected among different health care systems with each system using patient identifiers that are different than the identifiers used by the other health care systems. Furthermore, patient records collected within the same health care institution may use multiple identifiers for referring to the same patient. Still further, typographic errors, which happen routinely in the course of collecting patient information and are unavoidable, can result in inaccurate and inconsistent data about a single patient. In some instances, certain data collected about a patient, such as weight, body-mass-index (BMI), or height may be falsely reported. For example, a patient might underreport his or her true weight due to reasons of vanity. Ultimately, such inconsistencies lead to incomplete data sharing among health care professionals, patients, and data repositories.

Record linkage is the methodology of bringing together corresponding records from two or more files or finding duplicates within files. The term record linkage originated in the public health area when files associated with an individual patient were brought together using name, date-of-birth, and other information. Patient record linkage, or matching, is a key process for identifying and connecting records belonging to the same patient, including records created over extended time periods and across several disparate data sources.

A formal mathematical foundation for record linkage was proposed by Fellegi and Sunter, and uses a field-specific weight that is based on the agreement/disagreement between corresponding fields of data. In the Fellegi-Sunter (F-S) approach, two datasets A and B are matched by way of classifying pairs in a product space A×B from the two datasets A and B into M, a set of true matches, and U, a set of true non-matches.

To establish the match or nonmatch status of two records, the F-S method produces a composite likelihood ratio that is the sum of field-specific weights for each record-pair. The field-specific weight is based on a likelihood ratio whose numerator is the probability that a matching field agrees given the comparison pair is a true match; its denominator is the probability that a matching field agrees given that the comparison pair is a true non-match. This ratio reflects the relative importance of a comparison field in predicting match status. For example, agreement on date of birth receives a higher positive weight than agreement on sex, but disagreement on date of birth receives fewer penalties (a smaller negative weight) than sex receives for disagreement. The sum of all field-specific weights produces the composite match score for a pair.

While the F-S method may produce reasonably accurate results, it does not explicitly accommodate the notion of a value-specific weight or otherwise leverage the information contained in field-specific values. As a result, each field receives an identical agreement weight for all record pairs regardless of the relative importance of the specific values being compared for that field. Likewise, F-S does not take into account the information that is embodied in a time-series of records, including for example, the time intervals that separate serial episodes for entities that have experienced two or more episodes of activity that resulted in creating and storing records of the episodes.

Further limitations resulting in the F-S approach and prior attempts to provide record linkage include:

(1) Excessive false-negative rates, such as false misses or non-linkages, associated with spelling errors; fat-fingered entries, such as close-on-keyboard entries or replicated keystrokes; transpositions of digits in identifiers; aliases for first names; variable use of middle-name as first-name; deception/fraud involving use of a false name; transpositions of (first) given name and (last) family name; omissions (e.g., don't know or don't enter first or middle name); mishandling of records, for example records within-family, related to twins/triplets/octuplets/etc.; transpositions in date fields; invalid or out-of-date values, for example insurer/plan have lapsed and/or are no longer in-force; missing and/or anonymous data, for example an entry for John or Jane Doe with a SSN of 999-99-9999; omission of area code or zip-code; or other causes. In health care, such false-negatives generally lead to errors of omission: failures to implement the best treatment or other action. However, as in the case of allergy-checking or drug-drug interaction checking, false-negatives may also lead to errors of commission: undertaking a course of treatment that is harmful and that could have been interdicted had the true match been identified.

(2) Excessive false-positive rate (i.e., false linkages). False-positive linkage of entities that are not in fact the same person generally leads to errors of commission: undertaking a course of action that would have been beneficial for one of the entities but that is not beneficial for the other entity.

(3) Reliance on a higher number of variables to perform matching, which fails to achieve the desired sensitivity and specificity, chiefly because the rate of missingness for the extended-range variables is excessive.

Accordingly, it is therefore desirable to establish systems and methods for providing more accurate and efficient record linkage including using time-oriented information that is readily available for each of the records in the repository and for any new record for which a match in the repository is sought. Such record linkage technology, which is particularly useful when patient records lack any unique identifier, offers numerous benefits to physicians and health care organizations, not only by improving the quality of patient care, but also by facilitating clinical research and population-based studies. It is further important for the aggregating and integrating of health information.

SUMMARY

A system, methods, and computer-readable media are provided for facilitating record matching and entity resolution and for enabling improvements in record linkage including determining records that refer to the same entity or individual as one or more other records in a collection of records that are stored in a computer system and detecting matches of a new record with one or more others that already exist and are stored in online databases. In an embodiment, a phenotypic bit-vector "fingerprint" pattern-specific weight is incorporated into conventional record linkage methods to enhance the record linkage accuracy and statistical performance. In embodiment, a value-specific weight is calculated from the dichotomized values of selected phenotypic variables, and provides an opportunity to capture and measure the relative importance of specific values found in a field.

In another embodiment, a power-spectrum-based temporal pattern-specific weight may be incorporated into record linkage methods to enhance the record linkage accuracy and statistical performance. For example, a value-specific weight may be calculated from a population-based frequency of field-specific values and provides an opportunity to capture and measure the relative importance of specific values found in a field. A time-series-derived Bayesian power spectrum weight may be calculated from the population-based frequency of temporal pattern-specific values in terms of intensities at various frequencies of the power spectrum computed from the time-series, and further provides an opportunity to capture and measure the relative importance of specific sequences of care episodes.

In an embodiment, binary fingerprints are formed by (a) constructing bit-vectors ("fingerprints") by ascertaining memberships of a person in a population in terms of quantiles of phenotypic variables such as laboratory test values; (b) calculating similarities or distances for each such combination; (c) combining each pairwise similarity or distance with the corresponding conventional record-linkage weights, such as by using a root-mean-square, dot product cosine measure, or other suitable score; and (d) rank-ordering the resulting set according to the combined score.

In an embodiment, time series are formed by (a) provisionally appending a proband episode date-time stamp to those of records of other episodes for which conventional multivariate evidence exists favoring linkage of the proband to other previously linked episodes, (b) calculating Bayesian power spectra for each such combination, (c) repeatedly randomly sampling the spectra to calculate the median likelihood for each, with for example, Bonferroni or other suitable correction for time series length, (d) normalize the median likelihood values so as to be on a scale that is commensurate with the weights calculated by conventional record-linkage system and method, (e) combining each scaled median likelihood with the corresponding conventional record-linkage weights using, for example, a root-mean-square or dot-product cosine measure or other suitable score, and (f) rank-ordering the resulting set according to the combined score.

In such ways, embodiments of the invention provide advantages including more accurate, dynamic, and robust matching, and matching where limited data exists. Embodiments further offer numerous benefits to physicians and health care organizations, not only by improving the quality of patient care, but also by facilitating clinical research and population-based studies.

BRIEF DESCRIPTION OF THE DRAWINGS

Embodiments of the invention are described in detail below with reference to the attached drawing figures, wherein:

FIG. 3 depicts example outputs of an embodiment for resolving an entity;

FIG. 6A depicts a 6-bit fingerprint cross-correlations for an example in accordance with embodiments of the invention;

FIG. 6B depicts bit-densities of a 6-bit fingerprint and sub-vectors for an example in accordance with embodiments of the invention; and FIGS. 7A and 7B illustratively provide example embodiments of a computer program routine for determining bit-vector fingerprints in accordance with embodiments of the invention.

DETAILED DESCRIPTION

Figure 1A:
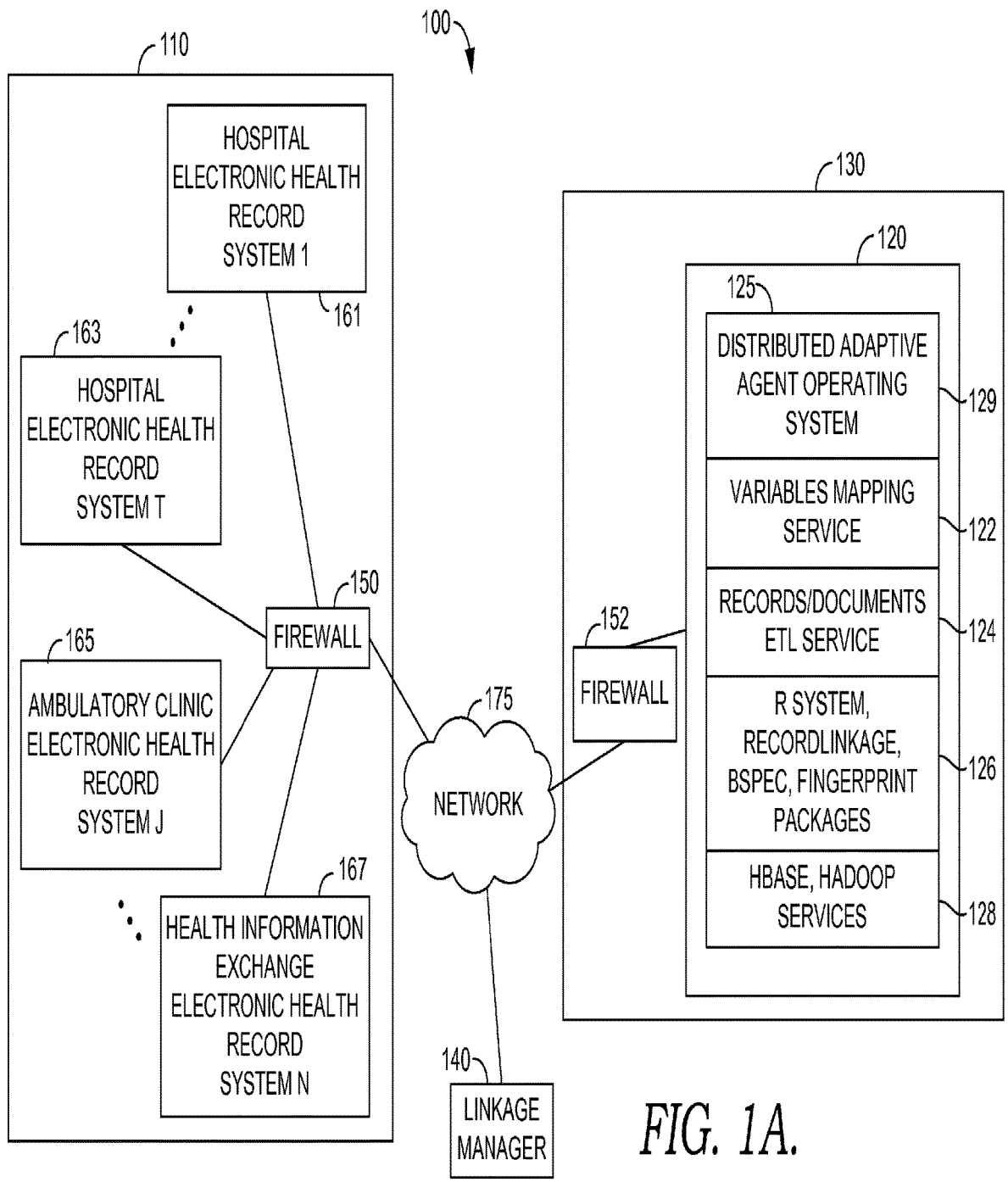
FIGS. 1A, 1B, and 1C depict aspects of an illustrative operating environment suitable for practicing embodiments of the invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer-readable storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other storage devices. These technologies can store data momentarily, temporarily, or permanently.

As discussed above, embodiments of the invention are provided for facilitating record matching and entity resolution by various methods and combinations of methods including incorporating power-spectrum-based temporal pattern-specific weighting into record linkage methods and incorporating phenotypic bit-vector "fingerprint" pattern-specific weight into record linkage methods to enhance the record linkage accuracy and statistical performance.

In an embodiment, health-care-related time series data are used for accurate and efficient record matching by extracting maximum amounts of information from short time series, which may occur infrequently. For example, a healthy patient may visit the doctor's office only once every several years, thereby resulting in a limited time series of information. By way of analogy, similar challenges are encountered by experimental astrophysicists who study gravitational waves. Out of necessity, these astrophysicists developed techniques that extract the maximum amount of information from short time series that arise from rare, brief events. Similar methodologies used in empirical identification of time series associated with gravitational waves can be fruitfully applied to the problem of identifying other short time series, including time series that arise in health and health care contexts.

For example, whenever two compact celestial objects, such as white dwarfs, neutron stars, or black holes, are in close orbit, they emit intense gravitational waves. Over time as the objects spiral closer to each other, the frequency and amplitude of this radiation increases, resulting in a swept-frequency pattern known as a "chirp." Gravitational waves have not yet been directly detected on Earth because of their extremely small effect on matter. But their existence can be inferred from changes in the orbital periods of the objects. For example, changes in the orbital periods of binary pulsars, such as PSR 1913+16. 'Orbital lifetime' is a characteristic property of celestial objects that are sources of gravitational radiation. Orbital lifetime determines the average number of binary stars (i.e., "binaries") in the universe whose gravitational waves are likely to be detectable. Short-lifetime binaries produce strong, readily-detectable gravitational radiation but are rare. Long-lifetime binaries, which are more numerous, emit gravitational waves that are weak and hard to detect.

Gravitational radiation detection is facilitated using a class of instruments such as LIGO ("Laser Interferometer Gravitational-Wave Observatory," a ground-based interferometer that comprises multiple observatories, separated over a geographical distance), which is most sensitive in the frequency band (30 Hz to 7 KHz) where two neutron stars are about to merge. The time frame for such a merger or coalescence of the objects lasts only a few seconds. Thus, LIGO or similar instruments must detect this "blink" of gravitational waves emitted over a few seconds out of a million-year orbital lifetime. It is calculated that only about once per decade or so does a coalescence of two neutron stars happen in a manner that could be detected by LIGO.

Current gravitational-wave detector design accounts for this very limited duration of data. There are approximately $3 \times 10$ msec per year, so even a fluctuation that has a probability of $10 \times 10^{10}$ of occurring is likely to occur in one year of data. In order to eliminate most false-positive signals, a signal-to-noise ratio threshold is used or, in some cases, multi-detector coincidence discrimination. However, concerning record linkage, there is no possibility of coincidence discrimination by multiple events synchronously incident upon two or more 'detectors'. Each event is incident upon only one facility. Therefore, some embodiments of the invention, which utilize methods similar to gravitational wave analytic methodologies, do not depend on multi-detector coincidence detection.

Furthermore, certain time-series analysis and forecasting methods are highly sensitive to the sequence in which events occur. For example, the frequency domain power spectrum of a time series $s(t)$ can accurately establish the probability of the identity of an object when ordinary human and time-series methods fail to identify the object correctly. The power spectrum of a classical symphony or other musical work reveals in each time segment the dominating key, through the pattern of spectral intensities at frequencies associated with fundamentals and harmonics. If the sections of the musical work are played in a different order, the power spectrum would not change, but the ear and the mind, which perform a time-frequency analysis, perceive a very different content than compared to how the original symphony is perceived. Therefore, to avoid excessive sensitivity to arbitrary differences in the sequencing of events, embodiments of the invention rely on frequency-domain power spectrum analysis methods to detect predominant frequencies and motifs.

On a finite segment of length delta-t, the resolution in frequency is 1/delta-t. We can give up fine resolution in frequency-space but, by so doing, gain information about when an event happened. Therefore, for some embodiments, rather than working in frequency-space with arbitrarily good resolution, we operate in the time-frequency plane, achieving a good compromise between the accuracy in frequency and the accuracy in time. This has advantages when we aim to detect transient phenomena, such as gravitational wave bursts or irregular alternations of patterns of health care activity (motifs) such as arise in conditions that undergo periods of exacerbation and remission, such as multiple sclerosis, lupus, rheumatoid arthritis, and inflammatory bowel disease.

In this regard, it is commonplace that people naturally experience 'epochs' in their personal health history. Each epoch is associated with characteristic patterns and rates of health services utilization. Relatively frequent utilization of health care is typical of infancy and young childhood, and the rate of utilization decreases for most young adults. For women of childbearing age, gynecologic exams and treatments follow distinctive patterns in western countries, as do pre-natal visits for uncomplicated pregnancy vs. complicated/high-risk pregnancy.

Elective surgeries and their subsequent follow-ups are another kind of 'motif.' The temporal event motifs of chronic conditions like cancer or hepatitis or HIV AIDS are distinct and different from motifs associated with chronic ambulatory-sensitive conditions such as heart failure, chronic obstructive lung disease, or diabetes. The motifs associated with declining health in the elderly are punctuate by 'ups-and-downs,' but the epochs' durations and successors are not, in general, as predictable as for the conditions noted for 'exacerbations-and-remissions.' Through power spectrum analysis methods, the offset of one epoch and the onset of a new epoch can often be detected from time series, within a span of 3 or 4 events, for example.

With regard to embodiments incorporating phenotypic bit-vector fingerprint(s) into conventional record linkage, an analogy may be drawn to medicinal chemists, who out of necessity, seek to identify new pharmaceutical compounds that may become clinically-effective candidates for drug development by performing distance-based, pharmacophore-oriented searching in combinatorial libraries comprised of many hundreds of thousands or event millions of compounds.

In health information exchanges (HIE) or other heterogeneous environments, patient records may not contain some result variables or may have historical intervals for which values are NULL. In an embodiment, it is a desirable design attribute that record-linkage routines have unbiased retrieval that is robust against this eventuality. In this connection, it is noted that the bit density in a fingerprint can affect its ability to retrieve similar items from a database primarily due to complexity effects. An embodiment approaches alleviating these effects by generating fingerprints that have a set-bit density of 50% or approximately 50%. In particular, a balanced-code approach to convert an ordinary binary fingerprint (whose bit density is not 50%) results in a fingerprint twice the length of the original with the right-padded half-vector synthetically bit-set to yield 50% bit density overall. In an embodiment, this step is optionally performed, but in an embodiment it is not necessary when outer tertiles are utilized. Bit-density balancing may be desirable in some embodiments where outer quartiles or other low-prevalence quantiles are used.

In an embodiment that includes comparing datasets using fingerprints, a dataset can be summarized by counting the frequency of occurrence of each set bit position. The frequency may be normalized by the number of fingerprints considered. Thus, a collection of N fingerprints can be converted to a single vector of numbers highlighting the most frequent set bits with respect to a given dataset. The bit spectra for two datasets (in particular, where the same types of fingerprints have been used) allows a comparison of the similarity of the datasets, without having to do full pairwise similarity calculation. In an embodiment, the difference between the structural features of the datasets can be quantified by evaluating the distance between the bit spectra. In particular, in an embodiment, bit spectra distance may optionally be used to prioritize which subsets of data shall be searched first, in circumstances that favor rapid return of high-quality matches or in circumstances when exhaustive searching of all datasets may not be feasible on account of time constraints, for example.

Turning now to FIG. 1A, there is presented in 100 an example operating environment suitable for practicing embodiments of the invention. Example operating environment 100 includes a computerized system for compiling and running an embodiment of a decision support recommendation service. With reference to FIG. 1A, a first premise location 110 includes a network behind firewall 150 communicatively coupled to Network 175. Premise location 110, which may comprise separate geographical locations, further includes one or more health record systems such as, for example, Hospital Electronic Health Record System 161, Hospital Electronic Health Record System 163, Ambulatory Clinic Electronic Health Record System 165, and Health Information Exchange Electronic Health Record System 167, each communicatively coupled to Network 175. In embodiments, Network 175 includes the Internet, a public network, or a private network. Embodiments of health record systems 161, 163, 165, and 167 include one or more data stores of health records and may further include one or more computers or servers that facilitate the storing and retrieval of the health records. Embodiments of health record systems 161, 163, 165, and 167 may further comprise a local or distributed network, which can include network 175, in some embodiments. Firewall 150 may comprise a separate firewall associated with each health record system, in some embodiments. Furthermore, in some embodiments, one or more of the health record systems may be located in the cloud or may be stored in data stores that are distributed across multiple physical locations. In some embodiments, one or more health record systems are communicatively coupled to the cloud, which may include or be communicatively coupled to network 175. In some embodiments, health record systems include record systems which store real-time or near real-time patient information, such as wearable, bedside, or in-home patient monitors, for example.

Continuing example operating environment 100 further includes computer system 120, which may take the form of a server, within premise 130, which is communicatively coupled through firewall 152 and network 175 to health record systems 161, 163, 165, and 167 in premise location 110, and also to linkage manager 140. In embodiments, linkage manager 140 may take the form of a software application operating on one or more mobile computing devices, tablets, smart-phones, front-end terminals in communication with back-end computing systems terminals, laptops, or other computing devices. In some embodiments, linkage manager 140 includes a web-based application or collection of applications that is usable to manage services provided by embodiments of the invention. In some embodiments, manager 140 comprises a Master Patient Index (MPI) manager and/or a Pseudo-MPI manager application.

Figure 1B:
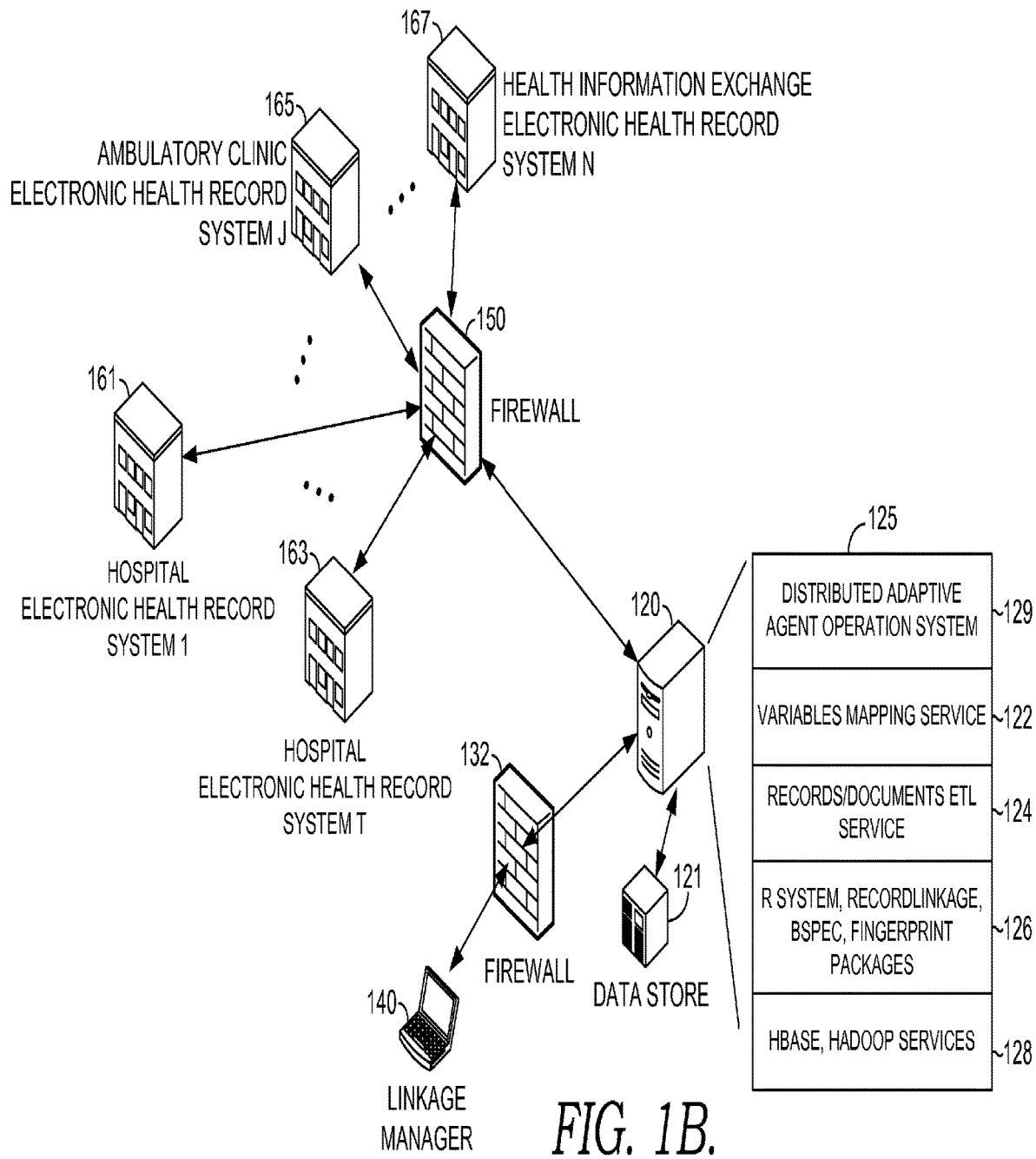

Embodiments of computer software stack 125 run on a computer system such as 120 shown in FIGS. 1A and 1B. Embodiments of software stack 125 may run as a distributed system on a virtualization layer within computer system 120. Embodiments of software stack 125 include a distributed adaptive Agent operating system 129 that can host a number of services such as 122, 124, 126, and 128. Embodiments of services 122, 124, 126, and 128 run as a local or distributed stack on a collection of personal computers and servers such as 120 and/or a computing device running manager 140. In one embodiment, manager 140 operates in conjunction with software stack 125. In embodiments, variables mapping service 122 and Records/Documents ETL service 124 provide services that facilitate retrieving frequent item sets, extracting database records, and cleaning the values of variables in records. Software packages 126 perform statistical software operations, and include statistical calculation packages such as, in one embodiment, the R system and R-system modules, and packages such as RecordLinkage, bspec for facilitating calculation of Bayesian power spectra or related statistical analyses, and fingerprint, for facilitating determination of phenotypic bit-vector fingerprints for time series data. An example embodiment employing software packages 126 is described in connection to FIG. 2, wherein a RecordLinkage package is associated with the steps at 240, bspec is associated with steps at 230, and fingerprint is associated with steps at 290. Additionally, one example embodiment of a computer program (here an R package) for fingerprint is illustratively provided in FIGS. 7A and 7B. Software packages 126 are associated with some embodiments of services 128. Embodiments of services 128 can include Apache Hadoop and H base framework that provide a distributed file system.

FIG. 18 illustratively depicts another aspect of an example operating environment. Some of the components of FIG. 18 are described above with respect to FIG. 1A. Also shown in FIG. 18 is data store 121, which in some embodiments includes patient data and information for multiple patients; variables associated with recommendations; recommendation knowledge base; recommendation rules; recommendations; recommendation update statistics; operational data store, which stores events; frequent itemsets (such as "X often happens with Y", for example) and itemsets index information; association rulebases, agent libraries, and other information, patient-derived data, health care provider information, for example. Although depicted as a single data store, data store 121 may comprise more than one data store, one or multiple locations, or in the cloud. The example operating environment of FIG. 1B also includes a firewall 132 between manager 140 and computer system 120.

Figure 1C:
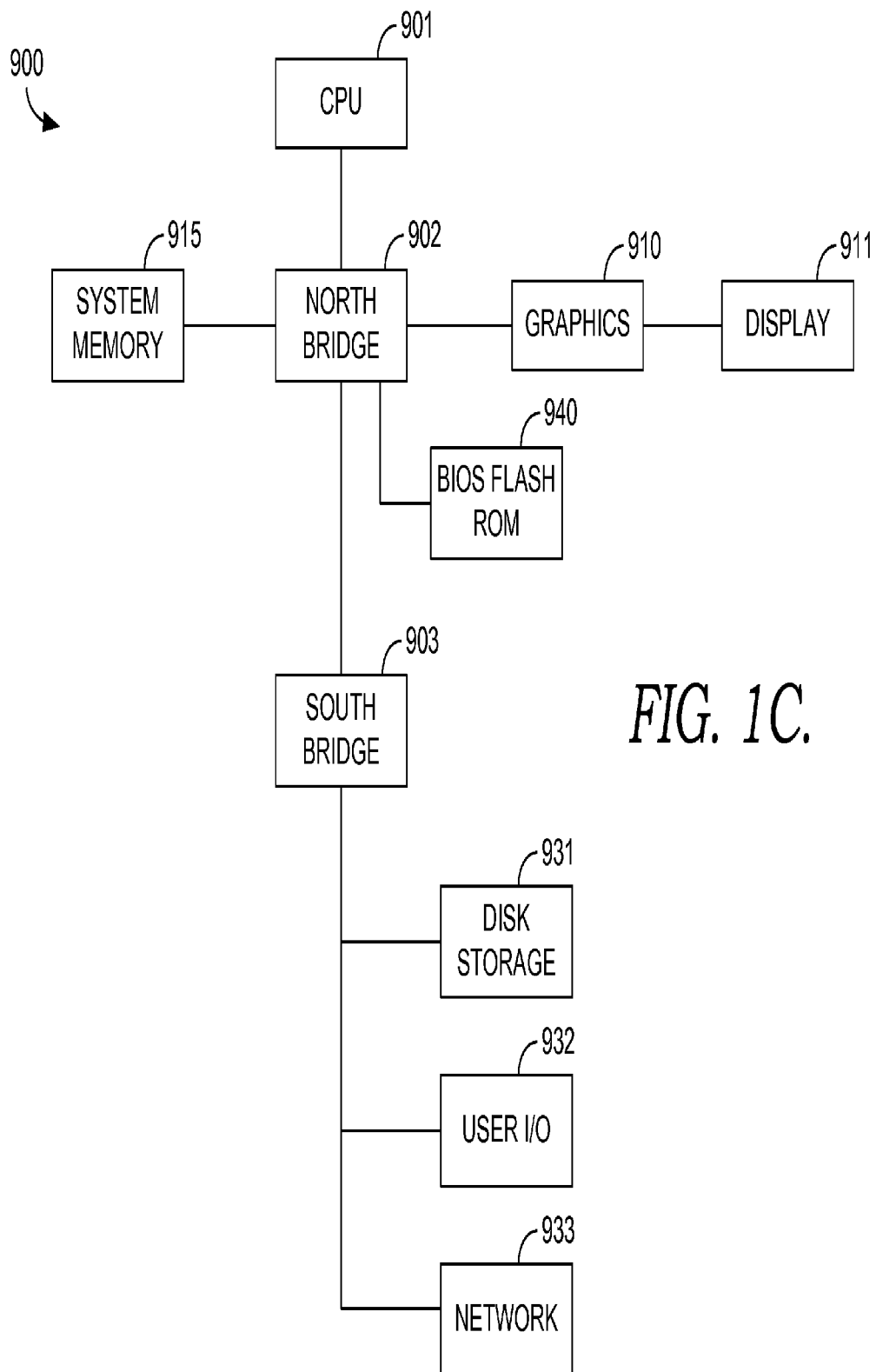

Turning now to FIG. 1C, there is shown one example of an embodiment of computer system 900 that has software instructions for storage of data and programs in computer readable media. Computer system 900 is representative of a system architecture that could be used for computer systems such as 120 and the computer device(s) operating manager 140. One or more CPU's such as 901 have internal memory for storage and couple to the North Bridge device 902, allowing CPU 901 to store instructions and data elements in system memory 915, or memory associated with graphics card 910 which is coupled to display 911. Bios flash ROM 940 couples to North Bridge device 902. South bridge device 903 connects to North Bridge device 902 allowing CPU 901 to store instructions and data elements in disk storage 931 such as a fixed disk or USB disk, or to make use of network 933 for remote storage. User 10 device 932, such as a communication device, a mouse, a touch screen, a joystick, a touch stick, a trackball, or keyboard, couples to CPU through South Bridge 903 as well.

In some embodiments, computer system 900 is a computing system made up of one or more computing devices. In an embodiment, computer system 900 includes an adaptive multi-agent operating system, but it will be appreciated that computer system 900 may also take the form of an adaptive single agent system or a non-agent system. Computer system 900 may be a distributed computing system, a centralized computing system, a single computer such as a desktop or laptop computer, or a networked computing system.

In some embodiments, computer system 900 is a multi-agent computer system with agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

Figure 4:
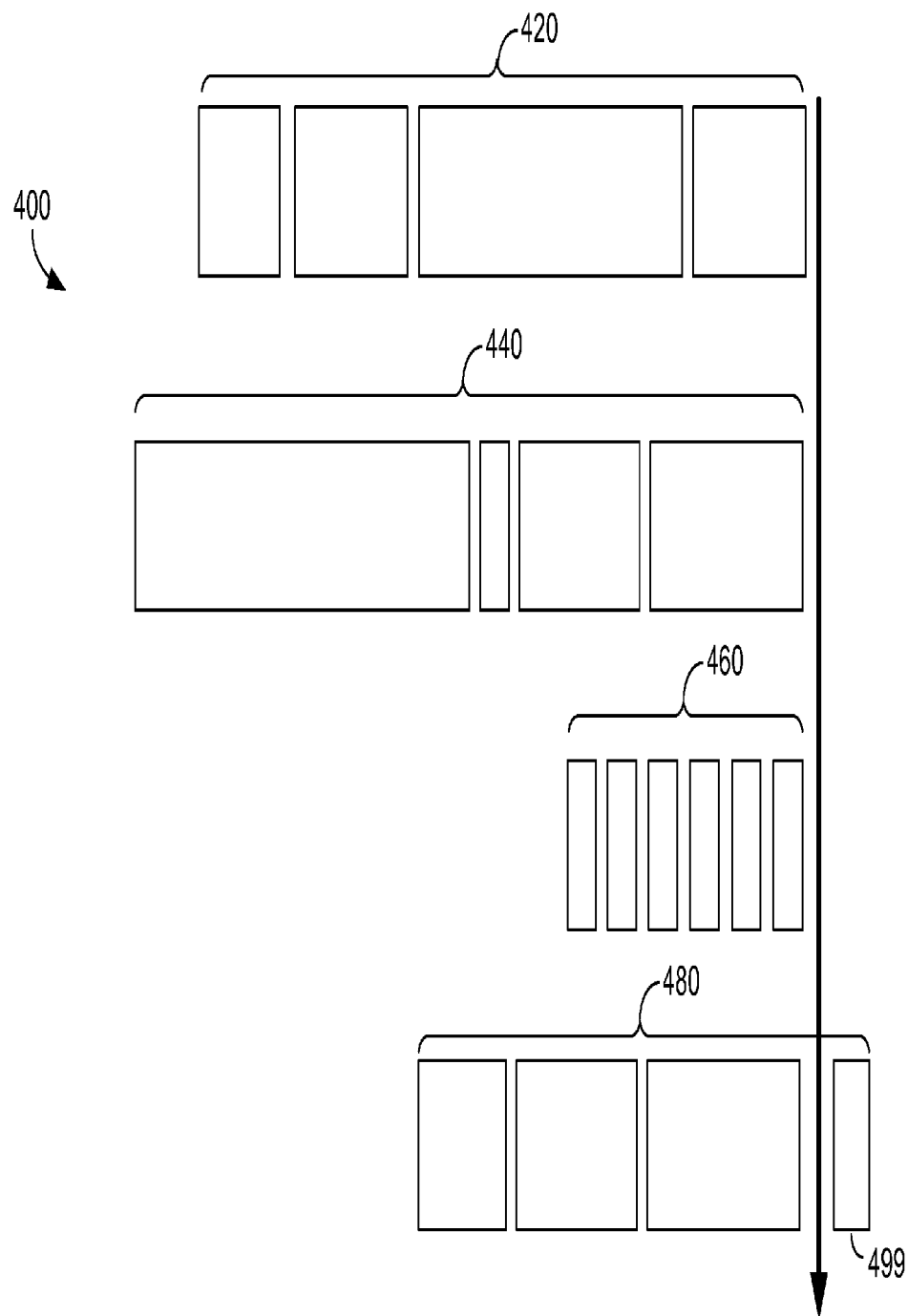
FIG. 4 depicts an illustrative representation of an embodiment for generating a set of plausible record linkages.

Turning now to FIG. 4, an illustrative representation of an embodiment for generating a set of plausible record linkages is depicted and generally referred to herein as 400. In the embodiment illustratively depicted in 400, patient data concerning "epochs" (e.g., sets of 3-4-visit episodes of patient care that is associated with characteristic patterns or rates of health service utilization) or other available sets of information about patient care episodes is accessed. Bars 420, 440, 460, and 480 represent serial episodes for 4 separate candidate cases for matching. For each candidate match, recent encounters and date-time coordinates of each encounter are accessed or determined, from available health records, and sorted in chronological order. It cannot be assumed, that at any given moment, each available health record system necessarily has received all of the updates concerning a patient in a timely or synchronous way. Some data about a patient may have been entered later in time, or not entered in a chronological order. For example, a health information exchange system in a particular state may have data about a patient that slowly trickles in due to administrative burdens for entering patient data. Thus, embodiments contemplate and account for the possibility that certain pieces of patient data may be leading or lagging each other in time.

Next, the current episode or record's date-time coordinates are inserted or appended to the most recent episode for current match-candidate cases. Embodiments of a date-time coordinate, or date-time information, can include date information, time information, or both date and time information. In some embodiments, candidate cases may be limited to patient cases that are determined to be a possible match by comparing other patient data variables, such as patient names, birth dates or age, gender, or similar variables that may be used to determine possible, but not necessarily determinative, matches. The time difference ("delta-t") between serial encounters is then determined and assembled as a time series. Accordingly, in embodiments, each time series represents a time difference between encounters. For example, a single time series vector may comprise 4 elements, each element representing the number of days since the previous health care visit by a patient who is a match candidate. In some embodiments, the time series is cast as an R datatype, for the R package, as described in connection to packages 126 of FIGS. 1A and 1B.

Next, in one embodiment, a power spectra for each time series is calculated. The likelihood of the spectra are then determined. In some embodiments, this is facilitated by permuting each spectrum multiple times using Bayesian Chain Monte Carlo simulation, from which a central tendency or median likelihood is determined. In some embodiments, a stable result is determined from performing at least 500 iterations.

In some embodiments, in conjunction or in additional to the above steps, a record linkage scoring weight is also determined by, for example, performing record linkage calculations based on demographic variables (such as census-type, slow moving variables (such as, for example, age, gender, race). Further, in some embodiments, F-S methods are used to determine this record-linkage weight.

In embodiments where a record linkage scoring weight is also determined, it is then combined with the power spectrum median weight, by for example RMS calculation or similar method for measuring distances such as, for example, cosine or correlation coefficient. The results of this combination are ranked, and a threshold is used to identify a positive (correct) match, shown as 499 in the example of FIG. 4. In embodiments, this threshold may be set based on the specific purpose of use. For example, a higher threshold may be in order in individual care scenario where significant harm would result from an improper match. Similarly lower thresholds may be set for scenarios unlikely to result in significant harm to a patient, such as epidemiological purposes.

Turning back to FIG. 2, a flow diagram is provided, which depicts an embodiment of a method for generating a set plausible record matches, and which is generally referred to herein as 200. At a step 205, bind the current entity of interest. In embodiments, the entity of interest represents a record of person or object for which candidate matches are sought. In some embodiments, method 200 may be used for matching objects, items, or data sets rather than people, such as, for example, inventoried equipment matching, matching objects associated with data entries, or data sets such as, for example, certain patterns of transactions, travel, or behavior. At a step 210, index hash values are calculated for blocking variables. Blocking variables can include variables such as birth day, birth month, birth year, or may also include variables in a specific context, such as whether the patient is a kidney patient, whether they're on dialysis, whether they've had prostate cancer, or whether they're diabetic, for example. In some embodiments, blocking variables may be used to determine how data sets are retrieved, when dealing with large-demographic data sets. Continuing with step 210, a plurality of independent demographic variables that are present in both a reference system and a target system associated with each entity, are selected to be used as blocking variables. In embodiments employing phenotypic bit-vector fingerprinting, step 210 of example method 200 includes identifying bitmap fingerprint variables.

At a step 215, for each M blocking variables, N instances are extracted to constitute a candidate matching table, where M and N are integers greater than or equal to zero. More specifically, from the target system, extract those database records containing lexically similar values for the selected blocking variables' values. In some embodiments, this step is facilitated using a hash table to establish the degree of similarity for retrieval. In embodiments employing phenotypic bit-vector fingerprinting, step 210 of example method 200 may include extracting from the target system the database records containing the phenotypic variable's values.

At a step 220, for each database entity retrieved, extract the date-time coordinates for the episodes that the retrieved records represent; compute inter-episode time intervals that separate the records in time; and assemble the intervals as time series associated with each record. In some embodiments, this time series comprises elements representing the time interval between episodes. For example, an example time series might include 5 numbers, each number representing the number of days or hours between episodes. Continuing with step 220, take the date-time coordinate associated with a candidate record to be matched and compute for each retrieved record the time interval that separates the candidate record from date-time stamp of the retrieved entity's most recent record. In embodiments employing phenotypic bit-vector fingerprinting, step 210 of example method 200 includes extracting P prior episode's bitmap fingerprint variables for the candidates.

In some embodiments, including some embodiments using bit-vector fingerprints, for each entity retrieved, a quantile membership is established each phenotypic variables associated with each record. In some embodiments, any quantile may be utilized. However, in the example reduced to practice and described in connection to FIGS. 5, 6A, and 6B, outer tertile memberships were used for purposes of forming binomial bit-vector fingerprints of each person and each candidate.

Following step 220, steps of method 200 proceed in three paths: steps related to determining Bayesian Power Spectra ("bspec") weights 230, which include steps 232, 234, 236, and 238, and steps related to determining RecordLinkage weights 240, which include steps 242, 244, and 246, and steps related to determining "fingerprint" weights 290, which include steps 292, 294, and 296. In embodiments, steps included in 290, 230, and 240 occur in parallel or sequentially. In some embodiments, only one, two, or all three paths are employed. For example, in an embodiment, only steps associated with 290 and 240 are utilized for record linkage. In an embodiment, the particular combination of paths 230, 290, and 240 to employ may be determined by the health-record information including the number of potential matches, the types of variables or health information available for use in the record linkage methods described herein, the purpose of the matching (e.g., exact match vs. pseudo-linkage used for research), and formatting and storage means implemented in the health records system(s).

In some embodiments, agents of a distributive adaptive agent operating system are dispatched to facilitate handling 290, 230, 240 or combinations of these. In some embodiments, agents may invoke other agents, as described above in connection to FIG. 1C. For example, a bspec agent might facilitate steps 232-238 and might invoke a second agent for the Bayesian power spectra calculations of step 234, and a third agent for the sorting and ranking in step 236.

Figure 2:
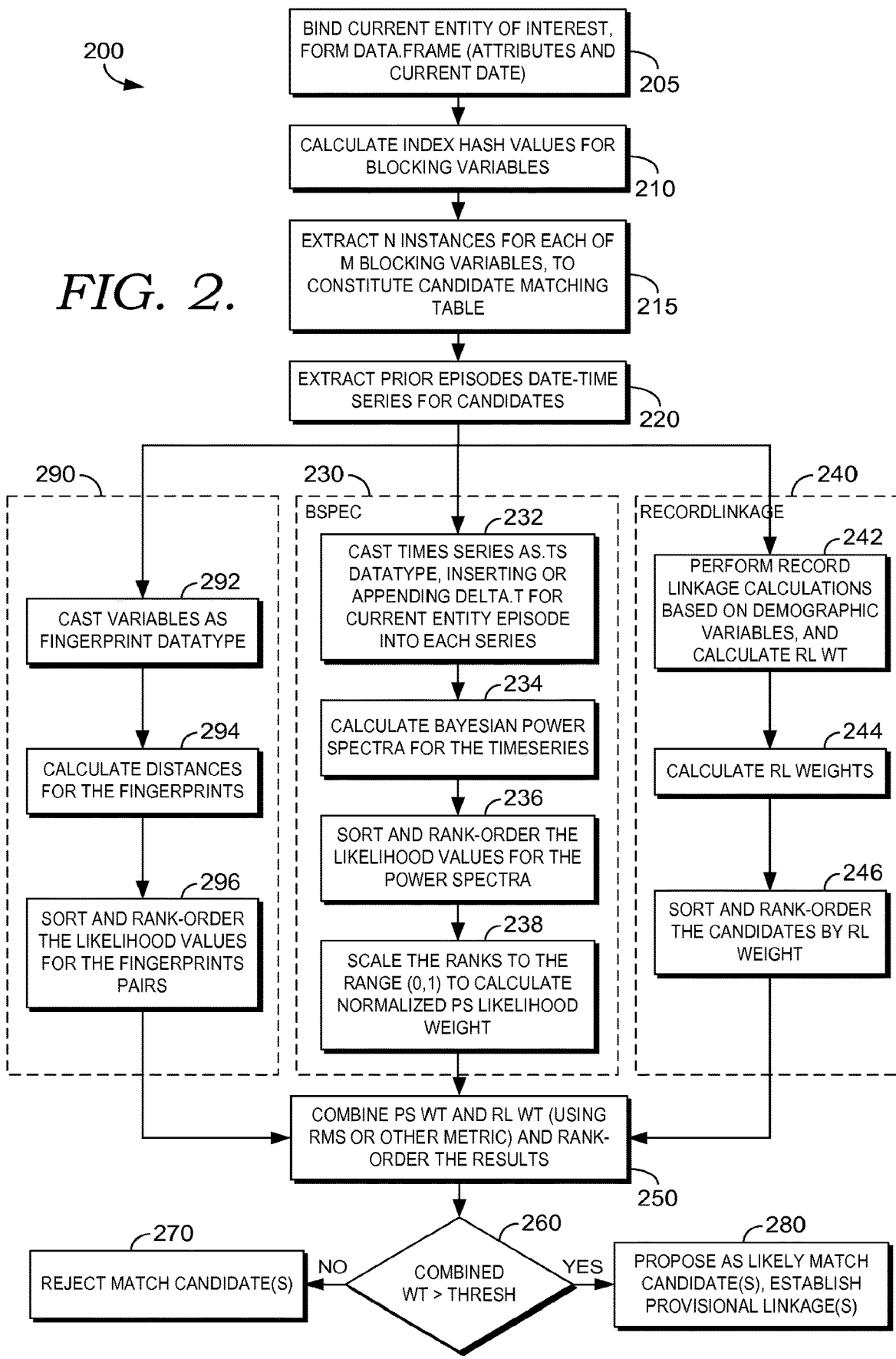
FIG. 2 depicts a flow diagram of an embodiment of a method for generating a set plausible record matches.

Continuing with FIG. 2, at a step 232, append the time interval as determined in step 220 to the time series for each retrieved entity. In some embodiments, the time series is cast as an R datatype, such as for example ".ts", for the R package, as described above in connection to packages 126 of FIGS. 1A and 1B. At a step 234, determine the power spectra for each time series from step 232. In some embodiments, the power spectra may be calculated on only a portion of the time series from step 232. For example, in embodiments, certain time series may be excluded based on the values of the elements, such as elements representing 0 days between episodes, negative or unusually high values, which might represent an error. Continuing with step 234, calculate the likelihood (probability) of each determined spectrum. In some embodiments, the likelihood of each spectrum is determined by iteratively permuting the spectrum and sampling the resulting permutations by Bayesian Markov Chain Monte Carlo simulation. In some embodiments, this simulation is performed for at least 500 iterations, retaining the median likelihood for each entity, to obtain a stable result.

At a step 236, median likelihood values determined in step 234 are sorted and ranked. At a step 238, the likelihood values are normalized to form a power spectrum weight ("PS_wt") for each entity. For example, in some embodiments, the likelihood values are normalized to lie within the range (0,1).

Turning now to the steps for determining Record Linkage weight 240, at a step 242 and 244, determine record linkage weight for each entity. In some embodiments, perform record linkage calculations on candidate record and the retrieved records, retaining for each a measure of numerical lexical similarity. In some embodiments, this may be facilitated by epiWeight or similar methods to form a record linkage weight (RL_wt) for each entity. In some embodiments, an opensource R record linkage software package may be used to facilitate forming a record linkage weight for each entity. In some embodiments, record linkage calculations are based on demographic variables, such as, for example, slow-moving variables or census-type variables. At a step 246, candidate matches are sorted and ranked by RL_wt.

Continuing with FIG. 2, at a step 292, cast variables as fingerprint datatype. In an embodiment, append the time interval as determined in step 220 to the time series for each retrieved entity. In some embodiments, the time series is cast as an R datatype, such as for example ".ts", for the R package, as described above in connection to packages 126 of FIGS. 1A and 1B. At a step 294, determine the distances for the fingerprints. In an embodiment, step 294 includes calculating the similarity of pairs of entities' bit-vector phenotypic fingerprints, by using, for example, the modified Tanimoto metric. Other example metrics that may be utilized include Hamming, Soergel, Pattern Difference, Tanimoto, Dice, Jaccard, Russel-Rao, Rodgers Tanimoto, Achiai, Carbo, Baroni-urbanibuser, Kulczynski2, Hamann, Yule, Pearson, Dispersion, McConnaughey, Stiles, Simpson, Petke, or Tversky, or other similar metrics such as is known to those practiced in the art. At a step 296, sort and rank-order the fingerprint similarity values.

At a step 250, bit-vector fingerprint similarity metrics (or "fingerprint weight") from steps associated with 290, power spectrum weights from steps associated with 230 and record linkage weights from steps associated with 240 are combined to form a composite score. In an embodiment, any combination of these weights (including the similarity metrics) is combined, for example, combinations with one, two, or all three of these weights. In some embodiments, the weights are combined by root-mean-square (RMS), cosine transform, correlation coefficient, or other similar means. In some embodiments, the combined weight is rank-ordered.

In some embodiments, median power spectrum likelihood determination from steps associated with 230, such as ascertained by Bayesian Markov Chain Monte Carlo simulation, may be treated as one biomarker or 'weight' that measures the similarity of record associated with the current entity to records from putative matching entities stored in the target database. Likewise, in steps associated with 240, a weight denoting degree of similarity that is calculated by record linkage methods, which may include those using F-S may be considered another biomarker. Furthermore, in some embodiments, where it may be difficult to find single biomarkers that perform with adequate accuracy, panels of biomarkers may be used such that a plurality of marker values are combined. In some embodiments, this is facilitated using linear combinations or decision-tree rule induction.

At a step 260, determine for the entity whether the composite weight score exceeds a threshold. In some embodiments, the threshold is a heuristic threshold. In some embodiments, the use case associated with the record linkage is used to determine the threshold. For example, in an epidemiological use, a lower threshold may be appropriate, but for individual care, where significant harm could result from a mistaken record linkage, a higher threshold may be used. In some embodiments, a health care provider may set the threshold; the threshold may be set from a table of associated use-cases for record linkages; or the threshold may be set based on the determined combined weights, for example, where there is a gap between successive rank-ordered combined weights. In some embodiments, an agent of a multi-agent computer system, such as 120 of FIGS. 1A and 1B, is used to set the threshold. In an embodiment, the threshold is 0.78. In an embodiment employing automatic matching, the threshold is set higher, such as 0.95.

At a step 270, entities having a composite score falling below the threshold are rejected as an improbable match that should not be linked with the candidate record. At a step 280, candidates with combined weights falling above the threshold are proposed as likely match candidates that merit consideration for linkage. In some embodiments, provisional linkages are audited before merging, for example, a health care provider or trained individual might review and confirm patient matches. In some embodiments, linkages may be determined as "pseudo-linkages" or linkages that are identified as probably matches without actually merging the records. These linkages may be used in certain use cases such as, for example, epidemiological studies. In some embodiments, use cases, such as certain epidemiological studies or other use cases, such as, for example, population research, may use persisting pseudo-linkages, which preserve provisional linkages.

In some embodiments, modified Tanimoto similarity determination from steps associate with 290, such as by fingerprint calculation, may be treated as one marker, indicator, or 'weight' that measures the similarity of a record associated with the current entity to records from putative matching entities stored in the target database. Likewise, in steps associated with 240, a weight denoting degree of similarity that is calculated by record linkage methods, which may include those using F-S, may be considered another "biomarker" or physiological indicator. Furthermore, in an embodiment, where it may be difficult to find a single physiological indicator that performs with adequate accuracy, panels of physiological indicators (or indicator variables) may be used such that a plurality of indicator or variable values are combined. In some embodiments, this is facilitated using linear combinations or decision-tree rule induction.

FIG. 3 provides an example output of an embodiment for resolving an entity and determining provisional linkage. In the example embodiment used in connection to FIG. 3, an entity resolver subsystem was reduced to practice using a server cluster running the Linux operating system, the open-source statistical software package R, and R modules bspec and RecordLinkage.

Records were randomly selected from a data warehouse, such as Cerner Health Facts®, which is derived from electronic health record (EHR) from 100% of episodes of care that are incident upon more than 130 U.S. based institutions. In this example, personally-identifiable information is removed in conformance with U.S. HIPAA law and regulations, and the de-identified data are stored in a separate, secure database. From a total of 50,000 encounters between 1 Jan. 2006 and 1 May 2011, a subset of 13,392 patients were identified who had 3 or more episodes during this time frame. An unrelated synthetic dataset of 10,000 names and birth dates was obtained.

Application of this embodiment using this data was able to correctly resolve 100% of the true linkages between example candidate records and the merged synthetic dataset, and exhibited 0% false-positive and 0.2% false-negative classifications.

Turning to FIG. 3, table 300 shows rows, including row 332, row 334, and rows 240 of candidate matches. Column variables 303 and 305 were supplied by the data warehouse. Variables 303 include patient-name related information and birth year (by), birth-month (bm), and birthday (bd). Variables 305 (columns v1 through v4) are days between visits, were the current patient-entity may be linked with the records shown in each row. In other words, if a current patient named "Michael Meyer" is visiting today and is to be linked with the MICHAEL MEYER record shown in the first row 332, then today's date (for visit #4) would be 187 days subsequent to the previous (v3) visit for that individual, which in turn was 168 days subsequent to the immediately prior visit (v2), and so on. Similarly, from today's date, it has been 60 days since Michael Myer (no "e") was last seen, as shown in column v4 of row 334. In this example, the first row might represent regular doctor checkups or routine visits, since the days are spread apart. The second row might represent a treatment because the time interval between visits is smaller.

In this example embodiment, values v1 through v4 for each row form a time series, with each time series comprising a vector with 4 elements (the values of v1, v2, v3, and v4). From the time series vectors, a Bayesian power spectrum weight (ps_wt) is determined for each entity row, as described above in connection to FIG. 2 and shown in column 309. Similarly, for each entity, a record linkage weight (rl_wt), shown in column 307, is determined for each row. Column 310 shows a combined composite weight of the rl_wt and ps_wt. In this example embodiment, RMS is used to determine the composite weight or score. Furthermore, here the scores are normalized to (0,1).

In this example, a threshold 320 is set at 0.75, indicating that the first two rows 332 and 334, which have composite scores (column 310) greater than the 0.75 threshold value, are true positive (i.e., correct) linkages. Remaining rows 340 represent the 18 nearest matches, out of the nearly 10,000 record test dataset. In this example embodiment, threshold 320 is determined by specificity and sensitivity. Here, sensitivity is set to 100% and specificity is set to 99.98%. (Entity linkage prevalence is equal to 0.12%.) These values are appropriate for use cases of individual patient care, where significant harm might occur due to a mistaken linkage. For epidemiological (or similar) purposes, specificity might equal 80%, and sensitivity might equal 95%.

Figure 5:
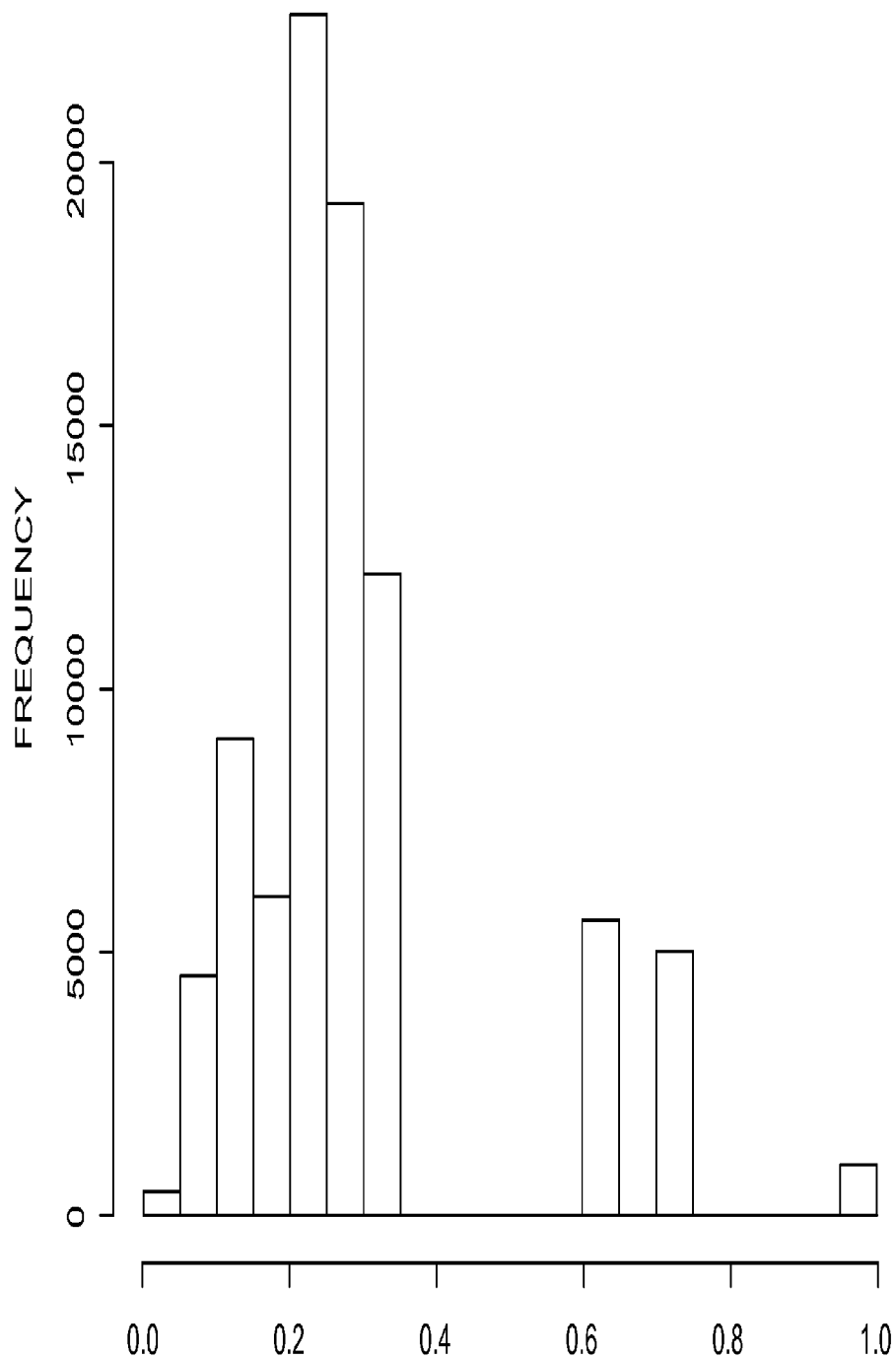
FIG. 5 depicts an example distance histogram 1-vector matched against a population of 100,000 candidates for an example in accordance with embodiments of the invention.

With reference to FIGS. 5, 6A, and 6B, a second example is provided for resolving an entity and determining provisional linkage using bit fingerprint(s). For the example embodiment used in connection to FIGS. 5, 6A, and 6B, an entity resolver subsystem was reduced to practice using a server cluster running the Linux operating system, the open-source statistical software package R, and R modules fingerprint and RecordLinkage. An example of one embodiment for the fingerprint module is illustratively provided in FIGS. 7A and 7B.

Continuing with this example, records were randomly selected from Cerner's Health Facts® data warehouse, which is derived from electronic health record (EHR) from 100% of episodes of care that are incident upon more than 130 U.S. based institutions. In this example, personally-identifiable information is removed in conformance with U.S. HIPAA law and regulations, and the de-identified data are stored in a separate, secure database. From a total of 200,000 encounters between 1 Jan. 2006 and 1 May 2013, a subset of 100,000 patients who had 3 or more episodes during this time frame were identified. Laboratory tests, including hemoglobin, serum creatinine, serum potassium, serum alanine aminotransferase, serum alkaline phosphatase, and serum albumin, were extracted. The population quantiles were calculated and the values for each episode of care for each person were dichotomized by outer tertiles. An unrelated synthetic dataset of 10,000 names and birth dates was obtained.

Application of this embodiment using this data was able to correctly resolve 100% of the true linkages between example candidate records and the merged synthetic dataset, and exhibited 0% false-positive and 0.2% false-negative classifications. The information illustratively provided in FIGS. 6A and 6B show 6-bit fingerprint cross correlations and bit-densities of the 6-bit fingerprint and sub-vectors, respectively, for this example. FIG. 5 illustratively provides a distance histogram wherein 1-vector is matched against the 100,000 candidates of the example. True matches (hits) can be seen on the far right-hand side of the histogram.

Another example for multi-variable record linkage by phenotypic bit-vector fingerprint is now described. The contents from two or more source systems, such as an EHR, frequently contain a plurality of episode records for each person. In each of the respective systems, the identity of the person associated with the episode records is known with certainty. However, the phenotypic information may fluctuate over time, between episodes or within episodes. For use-cases that have the aim of accurately matching and merging one or more corpuses of such records with another corpus, linking a plurality of records for each person in one system/corpus with a plurality of records for that person in one or more other systems/corpuses, it is feasible to assemble an array of pairwise similarity records computed as described above, determine a grand mean similarity for the array, and combine this episode-wise grand mean with the person-wise record-linkage RL similarity metric using root-mean-square (RMS) or other evidence-combining method as known to those practiced in the art. Furthermore, it is feasible to compute weighted mean, median, or similar representations that attach quantitative evidentiary strength to the association between System "A" 's plurality of records for the active person "X" and System "B" 's plurality of records for each candidate match person "Y" according to the phenotypic dispersion (for example, standard deviation of the similarity) and the sample size N that are present in the plurality of records. For example, one embodiment may calculate a lower prediction limit (LPL) of the mean modified Tanimoto distance:

$$50\% \ LPL = \max\left[0, d_{mT} - 0.67 * SD(d_{mT}) * \sqrt{1 + \left(\frac{1}{N}\right)}\right]$$

and apply RMS or other evidence-combining method to compute an aggregate similarity measure that may be embodied by the collections of records for "X" and "Y" that are extant in the two corpuses or systems. This embodies the lower certainty that is afforded by collections that exhibit substantial phenotypic within-person dispersion across episodes, as well as the effect of sample size. In particular, a person who has only a single exemplar episode record in one target system is accorded far lower weight in matching and record linkage, compared to persons who have low dispersion and many episode-related records.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the claims.

Some embodiments of the present invention include methods and computer readable media having computer-executable instructions embodied thereon for performing a method of identifying related records in a data store comprised of a plurality of records, the method comprising steps of: retrieving for each record a linkage indicator variable denoting whether the record is associated with one or more records for the individual or the same identity in the database; retrieving date-time information associated with each episode record; identifying blocking variables and using record linkage to creating a subset of plausibly-related records from the records in the data store; determining a power spectra likelihood weight for each record in the subset; determining a record linkage weight for each record in the subset; determining a composite score by combining the power spectra likelihood weight and record linkage weight; comparing the composite score to a threshold value; and if the composite score is greater than the threshold value, identifying a record as a related record, but if the composite score is less than the threshold, identifying the record as not related.

Some embodiments of the present invention include methods and computer readable media having computer-executable instructions embodied thereon for performing a method of identifying related records in a data store comprised of a plurality of records, the method comprising steps of: assigning a unique identifier to all records in the database that do not already have a unique identifier, the records arranged in rows and columns; retrieving for each record the linkage indicator variable denoting whether the record is associated with one or more records for the individual or the same identity in the database; retrieving the date-time stamps associated with each episode record; creating a blocking subset by conventional record linkage methods of between 1 and all of the columns in the database; creating a subset (s) consisting of the unique identifiers of records (r) from the database wherein the composite score combining the evidence from a record similarity measure and a power spectrum likelihood measure is greater than or equal to a heuristic value wherein the heuristic value is a positive real number, m; and outputting the unique identifiers of record matches identified by the pair-wise matching algorithm.

In some embodiments, a subset is not utilized, and a power spectra weight and record linkage weight are determined for each record in the record store. In some embodiments, the subset includes records for which episode-information comprising at least 3 visits or date-time entries is present.

Some embodiments further include wherein the applying a pair-wise matching algorithm step further comprises matching a candidate record X against records in the database. Some embodiments further include wherein the blocking subset of records has record linkage coefficients or weights computed, according to one of the methods as are commonly practiced by those experienced in the art, and the subset (s') of records whose weights exceed an heuristic value (RL_wt) is derived. Some embodiments further include wherein the most recent date-time coordinate of each record for the plurality of episodes Y in subset s' is subtracted from the date-time coordinate for the candidate record X to calculate a time difference, and this difference is appended to the time series of Y where the length of each such time series comprises not less than 4 time intervals.

Some embodiments further include wherein the time series comprises time intervals separating the episodes that are associated with the plurality of records are used to calculate a set of frequency-domain power spectra. Some embodiments further include wherein the power spectra are subjected to repeated random permutations of the spectral frequencies, determine a median likelihood for each entity. Some embodiments further include wherein the probabilistic likelihoods for the power spectra are computed by Bayesian Markov Chain Monte Carlo sampling.

Some embodiments further include wherein the set of likelihood values of are sorted and rank-ordered, and some of the embodiments further include wherein the ranks of the likelihoods are scaled by arithmetic means such that the scaled values are in the range (0,1) to produce a power spectrum weight (PS_wt) for each record.

Some embodiments further include wherein any combination of the record linkage weight, power spectra weight, or bit-fingerprint weight values are combined by a root-mean-square transformation, cosine transformation, or other suitable means of combining multiple numerical indices of similarity or lexical closeness, and the resulting score is associated with each record. Further, some embodiments include wherein the elements of this associated resulting score are sorted in decreasing score order.

In some embodiments, a method is provided for identifying duplicate records in a database comprised of a plurality of records arranged in rows and columns. The method comprises assigning a unique identifier to all records in the database that do not already have a unique identifier; retrieving for each record the linkage indicator variable denoting whether the record is associated with one or more records for the individual or the same identity in the database; retrieving the date-time stamps associated with each episode record; creating a blocking subset by conventional record linkage methods of between 1 and all of the columns in the database; creating a subset (s) consisting of the unique identifiers of records (r) from the database wherein the composite score combining the evidence from a record similarity measure and a power spectrum likelihood measure is greater than or equal to a heuristic value wherein the heuristic value is a positive real number, m; and outputting the unique identifiers of record matches identified by the pair-wise matching algorithm. In one embodiment of this method, the applying a pair-wise matching algorithm step further comprises matching a candidate record X against records in the database. In one embodiment of this method, the blocking subset of records has record linkage coefficients or weights computed, according to one of the methods as are commonly practiced by those experienced in the art, and the subset (s') of records whose weights exceed an heuristic value (RL_wt) is derived. In one embodiment of this method, phenotypic variables are selected, extracted, and transformed into binomial dichotomized values for construction of bit-vector "fingerprints" that are then subjected to pairwise calculation of a similarity metric, and may further include that the dichotomization is performed by computing population quantile memberships for each phenotypic variable, and further that the quantiles selected are outer tertiles or outer quartiles. In one embodiment of this method, the bit-vector fingerprints are of length between 6 and 128, in one embodiment the bit-vector fingerprints are of length between 12 and 24, and in one embodiment of this method, the set of similarity metric values are sorted and rank-ordered. In one embodiment of this method, RS_wt and PS_wt values are combined, and the resulting score is associated with each record in s', and in one embodiment may be combined using root-mean-square transformation or cosine. In one embodiment of this method the elements of s' are sorted in decreasing score order. In one embodiment of this method, the similarity metric comprises the modified Tanimoto metric.

What is claimed is:

1. A computer-implemented method of determining related records, the method comprising: retrieving a plurality of candidate health records, each candidate health record having one or more encounters, each of the one or more encounters associated with a date-time coordinate; for each candidate health record, sorting the one or more encounters in chronological order based on the date-time coordinates; determining a time difference between each serial encounter of the sorted one or more encounters, and assembling the time difference between each serial encounter as a time series; ranking the plurality of candidate health records; determining a candidate match for a first candidate health record and a second candidate health record of the plurality of candidate health records based on a threshold value applied to the ranked plurality of candidate health records; and merging a first candidate health record and a second candidate health record based on the candidate match.

2. The method of claim 1, wherein ranking the plurality of candidate health records comprises determining Bayesian Power Spectra weights for at least a portion of the time series.

3. The method of claim 2, wherein determining Bayesian Power Spectra weights comprises appending the time difference to the time series for each of the plurality of candidate health records.

4. The method of claim 3, wherein determining Bayesian Power Spectra weights further comprises determining a power spectra for each time series.

5. The method of claim 4, wherein determining Bayesian Power spectra weights further comprises calculating a probability of each determined spectrum.

6. The method of claim 5, wherein determining Bayesian Power Spectra weights further comprises based on calculating the probability of each determined spectrum, determining median probability values.

7. The method of claim 6, wherein determining Bayesian Power Spectra weights further comprises ranking and sorting the median probability values.

8. The method of claim 7, wherein determining Bayesian Power Spectra weights further comprises normalizing the probability values to form a power spectrum weight for each candidate health record.

9. The method of claim 1, wherein ranking the plurality of candidate health records comprises determining a record linkage weight for each candidate health record.

10. The method of claim 9, wherein ranking the plurality of candidate health records further comprises ranking and sorting each candidate health record by the record linkage weight for each candidate health record.

11. The method of claim 1, wherein ranking the plurality of candidate health records further comprises determining a binary fingerprint for each candidate health record of the plurality of candidate health records.

12. The method of claim 11, wherein ranking the plurality of candidate health records further comprises determining a distance between the determined binary fingerprints.

13. The method of claim 1, wherein ranking the plurality of candidate health records further comprises combining and ranking one or more of a fingerprint weight, a record linkage weight, or a power spectrum weight for each of the plurality of candidate health records.

14. One or more computer storage media having computer-executable instructions embodied thereon that, when executed by one or more processors, cause the one or more processors to perform a method for determining related records, the method comprising: retrieving a plurality of candidate health records, each candidate health record having one or more encounters, each of the one or more encounters associated with a date-time coordinate; for each candidate health record, sorting the one or more encounters in chronological order based on the date-time coordinates; determining a time difference between each serial encounter of the sorted one or more encounters, and assembling the time difference between each serial encounter as a time series; ranking the plurality of candidate health records; determining a candidate match for a first candidate health record and a second candidate health record of the plurality of candidate health records based on a threshold value applied to the ranked plurality of candidate health records; and merging a first candidate health record and a second candidate health record based on the candidate match.

15. The media of claim 14, wherein ranking the plurality of candidate health records comprises determining and combining one or more of a fingerprint weight, a record linkage weight, or a power spectrum weight for each of the plurality of candidate health records.

16. The media of claim 15, wherein determining the power spectrum weight for each of the plurality of candidate health records comprises: appending the time difference to the time series for each of the plurality of candidate health records; determining a power spectra for each time series; calculating a probability of each determined spectrum; based on calculating the probability of each determined spectrum, determining median probability values; and ranking and sorting the median probability values.

17. The media of claim 15, wherein determining the record linkage weight for each of the plurality of candidate health records comprises: ranking and sorting each candidate health record by the record linkage weight for each candidate health record.

18. The media of claim 15, determining the fingerprint weight for each of the plurality of candidate health records comprises: determining a binary fingerprint for each candidate health record of the plurality of candidate health records; and determining a distance between the determined binary fingerprints.

19. A search system for determining related records, the system comprising: one or more processors; and one or more computer storage media storing computer-useable instructions that, when used by the one or more processors, cause the one or more processors to: retrieve a plurality of candidate health records, each candidate health record having one or more encounters, each of the one or more encounters associated with a date-time coordinate; for each candidate health record, sort the one or more encounters in chronological order based on the date-time coordinates; determine a time difference between each serial encounter of the sorted one or more encounters, and assembling the time difference between each serial encounter as a time series; rank the plurality of candidate health records; determine a candidate match for a first candidate health record and a second candidate health record of the plurality of candidate health records based on a threshold value applied to the ranked plurality of candidate health records; and merge a first candidate health record and a second candidate health record based on the candidate match.

20. The system of claim 19, wherein ranking the plurality of candidate health records comprises determining and combining one or more of a fingerprint weight, a record linkage weight, or a power spectrum weight for each of the plurality of candidate health records.

* * * * *